(12) United States Patent
Bernard et al.

(10) Patent No.: US 6,274,364 B1
(45) Date of Patent: Aug. 14, 2001

(54) ISOLATED CATHEPSIN L TYPE CYSTEINE PROTEASES AND REDUCING INTERCORNEOCYTE COHESION/ PROMOTING DESQUAMATION THEREWITH

(75) Inventors: Dominique Bernard; Michel Kermici, both of Paris; Marie-Alix Bernard-Bourboulon, Noisy le Sec, all of (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/143,446

(22) Filed: Aug. 28, 1998

(30) Foreign Application Priority Data

Aug. 29, 1997 (FR) .................................. 97 10818

(51) Int. Cl.⁷ .................................... C12N 9/48
(52) U.S. Cl. .................................... 435/212
(58) Field of Search ............................ 435/212

(56) References Cited

U.S. PATENT DOCUMENTS 5,710,014   1/1998   Gottesman et al. ............... 435/68.1

FOREIGN PATENT DOCUMENTS

| 19619366 | 11/1997 | (DE) . |
| 2306961 | 5/1997 | (GB) . |
| 06192124 | * 7/1994 | (JP) . |
| 95/07686 | 3/1995 | (WO) . |

OTHER PUBLICATIONS

Reilly et al., "Synthesis and Processing of Cathepsin L, an Elastase, by Human Alveolar Macrophages", Biochem. J., 257(2), pp. 493–498, Jan. 1989.*
Mason et al., "Purification and Properties of Human Liver Cathepsin L", Biochem. Soc. Trans., 12(6), p. 1111, Dec. 1984.*
Mason et al., "Human Liver Cathepsin L", Biochem. J., 226(1), pp. 233–241, Feb. 1985.*
Mason et al., "the N–terminal Amino Acid Sequences of the Heavy and Light Chains of Human Cathepsin L. Relationship to a cDNA", Biochem. J., 240(2), pp. 373–377, Dec. 1986.*
Smith et al., "Activity and Deletion Analysis of Recombinant Human Cathepsin L Expressed in *Escherichia coli*", J. Biol. Chem., 264(34), pp. 20487–20495, Dec. 1989.*
Heidtmann et al., "Secretion of a Latent, Acid Activable Cathepsin L Precursor by Human Non–small Cell Lung Cancer Cell Lines", Proc Annu Meet Am Assoc Cancer Res, vol. 34, p. 77, Abstract 459, Mar. 1993.*
Baricos et al., "Human Kidney Cathepsins B and L. Characterization and Potential Role in Degradation of Glomerular Basement Membrane", Biochem. J., 252(1), pp. 301–304, May, 1988.*
Chauhan et al., "Cloning, Genomic Organization, and Chromosomal Localization of Human Cathepsin L", J. Biol. Chem., 268(2), pp. 1039–1045, Jan. 1993.*
Rao et al., "Expression and Localization of Cathepsin L in Human Gliomas (Meeting Abstract)", Proc Annu Meet Am Assoc Cancer Res, (1995). vol. 36, p. 95, Abstract 568, Mar. 1995.*
Reilly et al., "Uptake of Extracellular Enzyme by a Novel Pathway is a Major Determinant of Cathepsin L Levels in Human Macrophages", J. Clin. Invest., 86(1), pp. 176–183, Jul. 1990.*
A. Kawada et al: "Processing of cathepsins . . . " Archives of Dermatological Research, vol. 289, No. 2, Jan. 1, 1997, pp. 87–93.
S. Gal and M. Gottesman: "Isolation and sequence of a cDNA . . . " The Biochemical Journal, vol. 253, 1988, London, GB, pp. 303–306.

\* cited by examiner

*Primary Examiner*—Jon P. Weber
(74) *Attorney, Agent, or Firm*—Burns, Doane, Swecker & Mathis, L.L.P.

(57) ABSTRACT

A cathepsin L type cysteine protease has been isolated from the healthy stratum corneum of human skin. The protease has a pH optimum of 5 to 5.5 and mass of about 28 kDa.

11 Claims, 7 Drawing Sheets

ISOLATED CATHEPSIN L TYPE CYSTEINE
PROTEASES AND REDUCING
INTERCORNEOCYTE COHESION/
PROMOTING DESQUAMATION
THEREWITH

CROSS-REFERENCE TO PRIORITY APPLICATION

This application claims priority under 35 U.S.C. §120 of FR-97/10818, filed Aug. 29, 1997, assigned to the assignee hereof and hereby expressly incorporated by reference.

BACKGROUND OF THE INVENTION

1. Technical Field of the Invention

The present invention relates to certain isolated polypeptides, to mixtures of polypeptides derived from proteolysis of said isolated polypeptides, to compositions comprised thereof and to cosmetic treatments for reducing intercorneocyte cohesion, and, therefore, for promoting desquamation.

2. Description of the Prior Art

The skin constitutes a physical barrier between the body and its surroundings. It consists of two tissues: the epidermis and the dermis.

The dermis provides the epidermis with a solid support. It is also its feeder component. It consists principally of fibroblasts and an extracellular matrix itself principally composed of collagen, elastin and a substance deemed "ground substance," these components being synthesized by the fibroblast. Leucocytes, mastocytes or tissue macrophages are also found therein. It also comprises blood vessels and nerve fibers.

The epidermis is a desquamative pluristratified epithelium 100 μm thick on average and is conventionally divided into a basal layer of keratinocytes which constitutes the germinative layer of the epidermis, a so-called prickle cell layer consisting of several layers of polyhedral cells arranged on the germinative cells, a so-called granular layer including flattened cells containing distinct cytoplasmic inclusions, the keratohyalin granules, and, finally, a top layer designated the horny layer (or stratum corneum), including keratinocytes at the final stage of their differentiation, designated corneocytes. These are anucleated, mummified cells which are derived from the keratinocytes.

The corneocytes are principally composed of a fibrous matrix containing cytokeratins, surrounded by a very resistant structure 15 nm thick, designated horny or hornified envelope. The stacking of these corneocytes constitutes the horny layer which is responsible for the barrier function of the epidermis.

The stratum corneum possesses a selective permeability which, by controlling the loss of water, ensures a physiological hydration of the skin. It further constitutes a barrier against challenge from or attacks by the surroundings, whether chemical or physical. The stratum corneum is composed of two parts:

(1) the stratum corneum compactum whose cellular organization corresponds to a columnar stacking of the corneocytes above the granular cells from which they are derived. Each corneocyte exhibits maximum covering with the super- and subjacent corneocytes;

(2) the stratum disjunctum including the final strata of the horny layer which are less cohesive than the above and the site of desquamation of the corneocytes.

In the stratum corneum, the intercorneocyte space is filled with lipid sheets derived from lamellar bodies. Epidermal differentiation represents a continual and oriented maturation process which, from basal keratinocytes results in the formation of corneocytes which are completely keratinized dead cells. This differentiation is the result of perfectly coordinated phenomena which will lead to a constant thickness being maintained and which will thus ensure homeostasis of the epidermis. This passes via a regulation of the number of cells which enter the differentiation process and the number of cells which desquamate.

During the normal desquamation process, only the most superficial corneocytes become detached from the surface of the epidermis.

From the basal layer to the granular layer, cohesion is provided by the transcellular network defined by the desmosomes and the intermediate filaments of cytokeratins. This network is anchored onto the basal membrane by the hemidesmosomes.

In the horny layer, cohesion is provided by the intercellular structures derived from the desmosomes, designated corneosomes or corneodesmosomes, which firmly connect together the horny envelopes of the corneocytes. In the epidermis (non-palmoplantar), the corneodesmosomes are present over the entire corneocyte surface in the lower part of the horny layer, but just the peripheral corneodesmosomes persist in the upper part.

Recent studies have shown the key importance of the corneodesmosomes in intercorneocyte cohesion, as well as in the desquamation process. In particular, a close correlation exists between cell dissociation and proteolysis of certain corneodesmosomal components such as desmoglein I.

The study of desquamation makes it possible to demonstrate the existence of a fine biochemical regulation as far as the so-called "dead" layers of the epidermis. It is the enzymes produced in the deeper living layers which will act sequentially and in a complementary manner, resulting in the final release of the corneocytes at the skin surface.

The principal enzymes suspected of taking part in desquamation have been recently described. They belong to two families of enzymes: the glycosidases and the proteases. The proteases cannot act alone and a preliminary action of glycosidases desquamating sites of proteolysis appears to be necessary.

Proteases constitute the type of enzymes which is probably the most involved in desquamation. They are subdivided into four families:

(i) aspartic acid proteases comprising an aspartic acid residue at the active site thereof, (ii) serine proteases comprising a serine moiety at the active site thereof, (iii) cysteine proteases comprising a cysteine moiety at the active site thereof, and (iv) metalloproteases which most typically comprise a zinc atom at an active site thereof and sometimes a calcium atom.

Among these proteases, the cysteine proteases of lysosomal origin (cathepsins B, H and L) are without doubt the most active proteases in the human body. They are the ones which would participate in the daily renewal of an individual's proteins (from 200 to 300 g for an individual of 70 kg).

In this regard, WO-95/07,686 describes two (2) cysteine proteases of apparent molecular weights 34 to 35 kilodaltons.

Numerous pathological conditions of the skin are characterized by the production of a thick horny layer and by an abnormal desquamation, namely, by hyperkeratbsis. The latter may occur on any anatomical skin area and in a wide variety of clinical contexts. Its physiopathalogical substratum and its cause are varied.

By way of example, representative thereof are:
(a) xerosis (or dryness of the skin),
(b) ichthyoses,
(c) psoriasis,
(d) certain benign or malignant tumor lesions,
(e) reactive hyperkeratoses.

Other pathological conditions are characterized by transdifferentation or metaplasia, at the level of the mucosae, Malpighian or otherwise, but normally nonhornified, which become hornified, i.e., which become covered with an abnormal epithelium, producing a horny layer at its surface. Although the genital mucosae and those of the upper aerodigestive tracts are most often involved, these metaplasias may be seated in various anatomical areas. Exemplary thereof are:
(a) leukokeratosis of the uterine neck during prolapsus,
(b) buccal leukokeratoses,
(c) keratotic benign tumor lesions of the Malpighian mucosae.

Without wishing to be bound by or to any particular theory of the invention, it is considered that these pathological conditions may be linked to a qualitative or quantitative deficiency in enzymes suspected of participating in desquamation, including, in particular, proteases.

The purification and recognition of novel polypeptides involved in intercorneocyte cohesion, in particular of proteases, is one of the routes which could allow the production of new species for combating the effects of an excess or a deficiency of polypeptides, in particular of proteases, principally at the surface of the skin or of the mucosae.

SUMMARY OF THE INVENTION

Accordingly, a major object of the present invention is the provision of isolated polypeptides involved in intercorneocyte cohesion.

Thus, polypeptides involved in intercorneocyte cohesion have now unexpectedly been identified, isolated and purified via biochemical techniques, from a human epidermis.

The present invention therefore features isolated polypeptides, belonging to the cathepsin L type cysteine proteases family, having an apparent molecular weight ranging from 15 to 32 kilodaltons and an apparent isoelectric point ranging from 6 to 9.

DETAILED DESCRIPTION OF BEST MODE AND SPECIFIC/PREFERRED EMBODIMENTS OF THE INVENTION

More particularly according to the present invention, by "apparent molecular weight" is intended the molecular weight obtained for the polypeptide by comparing its electrophoretic mobility with those of standard proteins of known molecular weights on a polyacrylamide/sodium dodecyl sulfate gel, or, alternatively, by comparing the elution volume of the polypeptide with that of standard proteins of known molecular weights in exclusion chromatography (according to the techniques described in "Protein Purification", J-C. Janson and L. Ryden, VCH Publisher Inc, N.Y., 1989).

By "apparent isoelectric point" is intended the isoelectric point obtained for the polypeptide in comparison with that obtained for standard proteins of known isoelectric point in chromatofocusing experiments as described in "Protein Purification", J-C. Janson and L. Ryden, VCH Publisher Inc. N.Y., 1989.

The polypeptides of the invention may be of natural or synthetic origin. By "synthetic" is intended any polypeptide obtained chemically or by production in an organism after introducing into this organism the components necessary for this production.

The polypeptides of the invention may be derived from any possible origin, namely, either animal, in particular mammalian and even more particularly human, origin or plant origin or from micro-organisms (inter alia, viruses, phages or bacteria) or from fungi, without detriment as to whether it is present naturally or otherwise in the said organism of origin.

Preferably, the polypeptides of the invention are of natural origin, isolated from mammalian tissues, particularly from mammalian skin.

Preferably, the polypeptides of the invention are isolated from human skin and even more preferably from human epidermis.

As indicated above, intercorneocyte cohesion is apparently due, inter alia, to the existence, in the horny layer, of polypeptides specific to the structures involved in the intercorneocyte junction.

Accordingly, the polypeptides of the invention are present in the horny layer and play a role in reducing intercorneocyte cohesion by breaking down the structures involved in the intercorneocyte junction, particularly of the corneodesmosomes.

It too is known that the polypeptides and, in particular, the enzymes, including the proteases, may be provided in a so-called mature form which corresponds to a primary amino acid sequence compatible with their activity. However, it is also known that these mature polypeptides are often derived, by a maturation phenomenon, from polypeptides of a larger size, precursors, which contain, in their primary amino acid sequence, the primary sequence of the mature polypeptide. The same may be true for the polypeptides of the invention.

Accordingly, this invention also features polypeptides in part comprising the polypeptides of the invention.

It is also known that the polypeptides may undergo post-translational modifications such as the formation of disulfide bonds, specific proteolytic cleavages, the addition of carbohydrates (glycosylation), phosphorylation, in particular at the level of the serines and/or of the threonines and/or of the tyrosines, and/or combination with lipids.

The invention therefore more particularly features the polypeptides of the invention,whether or not subjected to post-translational modifications.

The polypeptides of the invention may have been subjected to one or more post-translational modifications.

Preferably, the polypeptides according to the invention are glycosylated and/or phosphorylated.

The polypeptides of the invention have an apparent molecular weight ranging from 15 to 32 kilodaltons and preferably from 25 to 30 kilodaltons.

It is well known that enzymes, in general, and proteases, in particular, exhibit a maximum activity in media with a defined pH.

Accordingly, the polypeptides of the invention are characterized by a maximum activity at a pH ranging from 2 to 9, preferably from 3.5 to 6.5. For example, the maximum activity of the polypeptide on casein is at a pH ranging from 4.6 to 5.6.

It is also known to this art that the primary amino acid sequence of a polypeptide determines sites specifically recognized by proteases which, once the recognition of these sites has been achieved, will, with or without attachment to the said polypeptide, induce its cleavage by proteolysis.

Accordingly, the present invention also features at least one proteolysis fragment of the subject polypeptides.

Herein, by the term "polypeptide" is intended the natural or synthetic polypeptide of the invention or at least one of its fragments, whether obtained by proteolysis or by synthesis.

Intercorneocyte cohesion is apparently due to the existence, in the horny layer, of polypeptides specific to the structures involved in the intercorneocyte junction. It has been determined that certain hyperkeratotic pathologies could be associated with an excessive intercorneocyte cohesion.

Thus, it has now unexpectedly and surprisingly been determined that the polypeptides of the invention are involved in the phenomena for destroying the structures comprising the intercorneocyte junction and therefore in the intercorneocyte cohesion. The polypeptides of the invention are therefore useful in cosmetic or pharmaceutical compositions for reducing intercorneocyte cohesion and, hence, for promoting Accordingly, this invention also features cosmetic or pharmaceutical compositions comprising, in a physiologically acceptable medium (vehicle, diluent or carrier), at least one polypeptide as described above.

Preferably, the compositions of the invention are topically applied to the skin or the mucosae.

The present invention also features pharmaceutical compositions comprising at least one of the subject polypeptides for treating desquamation disorders, such as hyperkeratoses, for example xerosis (or dryness of the skin), ichthyoses, psoriasis, hyperkeratosis of certain benign or malignant tumor lesions, and reactive keratoses.

And the present invention also features pharmaceutical compositions comprising at least one of the subject polypeptides, for treating pathological conditions which are characterized by transdifferentiation or metaplasia, at the level of mucosae, Malpighian or otherwise, but normally nonhornified, which become hornified such as, for example, leukokeratosis of the uterine neck during prolapsus, buccal leukokeratoses, or benign or malignant hyperkeratotic tumor lesions of the Malpighian mucosae.

The amount of polypeptide contained in the composition of the invention of course depends on the desired effect and may therefore vary to a large extent.

To provide an order of magnitude, the composition may contain the polypeptide of the invention in a quantity representing from 0.00001% to 50% of the total weight of the composition and, preferably, in a quantity representing from 0.001% to 10% of the total weight of the composition, and still more preferably, in a quantity representing from 0.1% to 1% of the total weight of the composition.

In the prior art, certain compounds are described as protease activators. The beneficial effect of glycerol on xeroses is, for example, known, which effect is explained by an activating effect on the enzymatic systems, due to its hydrating action through which it is thought to promote the action of proteases which break down the corneodesmosomes and hence the desquamation (WO-95/07687).

Urea, and its derivatives, have also long been known to improve the surface condition of very dry and even ichthyotic skins (Swanbeck, *Acta Dermatologica and Venereologica*, 1968, 48,(123–127). Wiederanders et al., *Biomedical Biochemistry Acta*, 1986, 45, (11–12) (1477–1483)), have shown that a cathepsin extracted from fish is more active in the presence of urea. These authors have thus succeeded in assaying specifically cathepsins L and D whose activity is multiplied by a factor of 2.5 and 6, respectively, in the presence of urea.

Reducing agents are also described as protease activators. Representative thereof are, for example, sulfides, thiols such as dithiothreitol or trithiohexitol, cysteine, N-acetylcysteinee, proteins or protein hydrolysates high in cysteine, mercaptoethanol, thioglycerol, thioalkanoic acids and mercaptocarboxylic acids and analogs thereof such as, for example, mercaptosuccinic acid, thiolactic acid, thioglycolic acid and salts thereof, coenzyme A or reduced glutathione (GSH).

These reducing agents may be present in the composition in their active form or in the form of precursors thereof such as, for example, oxothiazolidine carboxylate which is a precursor of the cysteines.

Ethylenediaminetetraacetic acid (EDTA) is known to prevent the inactivation, by heavy metals, of the proteases, particularly of the cathepsin type. As such, EDTA is considered as a protease activator.

It is also possible to assimilate transglutaminases with a protease activator. These enzymes belong to the family of transpeptidases. They are calcium-dependent and catalyze the formation of isopeptide bridges $\epsilon$ ($\gamma$-glutamyl)lysine: reaction of the carboxyl group (on the $\gamma$ carbon) of the glutamine residue and of the amino group of a lysine residue or of a polyamine. Transglutaminases exist in two principal forms in the epidermis: cytosolic transglutaminase E (or epidermal) of MW 50–56 kD having a 70 kD precursor, and membrane transglutaminase K or type I of MW 92 kD. Transglutaminases E and K are both involved in the formation of the horny envelope by bridging numerous proteins to one another, of which the principal ones are involucrine, loricrine, elafine, cystatins, pancornulines (or SPR: Small Proline Rich), cytokeratins, desmoplakins I and II, desmogleins and corneodesmosine.

Cystatins are proteins which possess cysteine protease inhibiting activity (Takahashi et al.,*FEBS Letters*, 1990, 2, 261–264).

Accordingly, if the activity of the transglutaminases is increased either by the provision of transglutaminase activator, or by the direct provision of transglutaminase, the quantity of constituent proteins of the horny envelope is then increased, which proteins are trapped in the formation of this envelope under the influence of transglutaminase. The stratum corneum is in this case deprived of its endogenous proteins, including in particular the cystatins. The disappearance of the cystatins from the epidermis and more particularly from the stratum corneum then has the effect of releasing the cysteine proteases whose activity is then increased, which has the effect of reducing intercorneocyte cohesion and therefore of promoting desquamation.

Thus, this invention also features cosmetic or pharmaceutical compositions comprising at least one of the subject polypeptides, and, in addition, at least one protease activator.

Exemplary protease activators include glycerol, urea, EDTA, transglutaminase and reducing agents.

The quantity of protease activator contained in the composition of the invention of course depends on the desired effect and may therefore vary to a large extent.

To provide an order of magnitude, the composition may contain the protease activator in a quantity representing from 0.00001% to 15% of the total weight of the composition and, preferably, in a quantity representing from 0.001% to 10% of the total weight of the composition.

In a composition according to the present invention, the protease activators may be alone or in the form of a mixture.

Whatever their nature, the compositions of the invention may be ingested, injected or topically applied to the skin (over any skin area of the body) or the mucosae (buccal, jugal, gingival, genital, conjunctival and the like).

Depending on the mode of administration, the compositions according to the invention may be provided in any of the galenical forms conventional to this art.

For topical application onto the skin, the composition may take the form, in particular, of an aqueous or oily solution or of a dispersion of the lotion or serum type, of emulsions of liquid or semiliquid consistency of the milk type, obtained by dispersion of a fatty phase in an aqueous phase (O/W) or conversely (W/O), or of suspensions or emulsions of soft consistency of the aqueous or anhydrous cream or gel type, or of microcapsules or microparticles, or of vesicular dispersions of the ionic and/or nonionic type or of foams or alternatively in the form of aerosol compositions also comprising a pressurized propellant. These compositions are formulated according to conventional techniques.

For injection, the composition may be provided in the form of an aqueous or oily lotion or in the form of a serum. For the eyes, it may be provided in the form of drops, and for ingestion, it may be provided in the form of capsules, granules, syrups or tablets.

The quantities of the various constituents of the compositions according to the invention are those conventional in the fields considered.

These compositions constitute, in particular, cleansing, protective, treatment or care creams for the face, for the hands, for the feet, for the large anatomical folds or for the body, (for example day creams, night creams, makeup removing creams, foundation creams, antisun or sunscreen creams), fluid foundations, makeup removing milks, protective or care body milks, antisun or sunscreen milks, after-sun milks, skin care lotions, gels or foams, such as lotions for cleansing, antisun or sunscreen lotions, after-sun lotions, artificial tanning lotions, bath compositions, deodorant compositions containing a bactericidal agent, aftershave gels or lotions, depilatory creams, compositions against insect bites, analgesic compositions or compositions for treating certain skin diseases and afflictions such as eczema, rosacea, psoriasis, lichens, severe pruritus and ichthyosis.

The compositions according to the invention may also be formulated as solid preparations constituting cleansing soaps or cakes.

The compositions may also be packaged in the form of an aerosol composition, also containing a pressurized propelling agent.

The compositions according to the invention may also be formulated as a composition for the care of the scalp, especially a shampoo, a hair setting lotion, a treatment lotion, a hair styling cream or gel, a dyeing (especially oxidation dyeing) composition optionally in the form of dyeing shampoos, restructuring lotions for the hair, a permanent waving composition (especially a composition for the first stage of a permanent waving), a lotion or gel against hair loss, an antiparasitic shampoo, antidandruff compositions and the like.

The subject compositions may also be for dentibuccal use, for example a toothpaste. In this case, the composition may contain customary adjuvants and additives for compositions for buccal use and especially surfactants, thickening agents, humectants, polishing agents such as silica, various active ingredients such as fluorides, in particular sodium fluoride, and optionally sweetening agents such as sodium saccharinate.

When the composition is an emulsion, the proportion of fatty phase may range from 5% to 80% by weight, and preferably from 5% to 50% by weight relative to the total weight of the composition. The oils, waxes, emulsifiers and coemulsifiers used in the composition in the form of an emulsion are selected from among those conventionally used in the cosmetic field. The emulsifier and the coemulsifier are advantageously present in the composition in a proportion ranging from 0.3% to 30% by weight, and preferably from 0.5 to 20% by weight relative to the total weight of the composition. The emulsion may, in addition, contain lipid vesicles.

When the composition is an oily gel or a solution, the fatty phase may represent more than 90% of the total weight of the composition.

In known fashion, the cosmetic composition may also contain additives and adjuvants common to the cosmetic arts, such as hydrophilic or lipophilic gelling agents, hydrophilic or lipophilic additives, preservatives, antioxidants, solvents, perfumes, fillers, screening agents, odor absorbers and colorants. The quantities of these various adjuvants and additives are those conventional in the cosmetic field, and range, for example, from 0.01% to 10% of the total weight of the composition. These additives and adjuvants, depending on their nature, may be introduced into the fatty phase, into the aqueous phase and/or into the lipid spherules.

Exemplary oils or waxes which can be formulated into the compositions of the invention include mineral oils (petroleum jelly), vegetable oils (liquid fraction of shea butter, sunflower oil), animal oils (perhydrosqualene), synthetic oils (Purcellin oil), silicone oils or waxes (cyclomethicone) and fluorinated oils (perfluoropolyethers), beeswaxes, carnauba or paraffin waxes. Fatty alcohols and fatty acids (stearic acid) may be added to these oils.

Exemplary emulsifiers of the invention include glycerol stearate, polysorbate 60 and the PEG-6/PEG-32/glycol stearate mixture marketed under the trademark Tefose® 63 by Gattefosse.

Exemplary solvents according to this invention include the lower alcohols, especially ethanol and isopropanol, propyleneglycol.

And exemplary hydrophilic gelling agents which can be formulated into the compositions of the invention include the carboxyvinyl polymers (carbomer), acrylic copolymers such as acrylate/alkylacrylate copolymers, polyacrylamides, polysaccharides such as hydroxypropylcellulose, natural gums and clays, and exemplary lipophilic gelling agents include the modified clays such as bentones, metal salts of fatty acids such as aluminum stearates and hydrophobic silica, ethylcellulose, polyethylene.

The subject compositions may contain other hydrophilic active agents, such as proteins or protein hydrolysates, amino acids, polyols, urea, allantoin, sugars and sugar derivatives, water-soluble vitamins, plant extracts and hydroxy acids.

Representative lipophilic active agents include retinol (vitamin A) and derivatives thereof, tocopherol (vitamin E) and derivatives thereof, essential fatty acids, ceramides, essential oils, salicylic acid and derivatives thereof.

According to the invention, the subject compositions may combine at least one extract of at least one Iridaceae with other active agents intended especially for the prevention and/or treatment of skin conditions. Exemplary such active agents include:

(a) agents reducing skin differentiation and/or proliferation and/or pigmentation such as retinoic acid and isomers thereof, retinol and esters thereof, vitamin D and derivatives thereof, estrogens such as oestradiol, kojic acid or hydroquinone;

(b) antibacterials such as clindamycin phosphate, erythromycin or antibiotics of the tetracycline class;

(c) antiparasitic agents, in particular metronidazole, crotamiton or pyrethroids;

(d) antifungal agents, in particular the compounds belonging to the imidazole class such as econazole, ketoconazole or miconazole or their salts, the polyene compounds, such as amphotericin B, the compounds of the allylamine family, such as terbinafine, or octopirox;

(e) antiviral agents such as acyclovir;

(f) steroidal anti-inflammatory agents such as hydrocortisone, betamethasone valerate or clobetasol propionate, or nonsteroidal anti-inflammatory agents such as, for example, ibuprofen and salts thereof, diclofenac and salts thereof, acetylsalicylic acid, acetaminophen or glycyrrhetinic acid;

(g) anaesthetic agents such as lidocaine hydrochloride and derivatives thereof;

(h) antipruritic agents such as thenaldine, trimeprazine or cyproheptadine;

(i) keratolytic agents such as α- and β-hydroxycarboxylic or β-ketocarboxylic acids, their salts, amides or esters and more particularly hydroxy acids such as glycolic acid, lactic acid, salicylic acid, citric acid and, in general, fruit acids and 5-n-octanoylsalicylic acid;

(j) moisturizing agents such as glycerol and its derivatives;

(k) anti-free-radical agents, such as α-tocopherol or esters thereof, superoxide dismutases, certain metal chelators or ascorbic acid and esters thereof;

(l) antiseborrhoeic agents such as progesterone;

(m) antidandruff agents such as octopirox or zinc pyrithione;

(n) anti-acne agents such as retinoic acid or benzoyl peroxide;

(o) extracts of plant or bacterial origin.

Accordingly, in a specific embodiment of the invention the composition also comprises at least one agent selected from among antibacterial, antiparasitic, antifungal, antiviral, anti-inflammatory, antipruritic, anaesthetic, keratolytic, anti-free-radical, antiseborrhoeic, antidandruff and anti-acne agents, and/or agents reducing skin differentiation and/or proliferation and/or pigmentation.

Too, this invention features a cosmetic regime or regimen for combating excessive intercorneocyte cohesion and therefore for increasing desquamation, which techniqdue comprises topically applying to the skin a cosmetic composition comprising at least one polypeptide of the invention.

This invention also features the use of the subject polypeptides to prepare or purify, optionally from the epidermis, any structural or functional molecule capable of specifically binding to said isolated polypeptide or to said isolated proteolysis fragments or to the said synthetic peptide. This molecule may in particular correspond to other structural proteins specific to the corneodesmosomes and various enzymes of the horny layer, of the "protease," "glycosidase" or "phosphatase" type.

The present invention lastly features the use of the subject polypeptides to prepare specific monoclonal antibodies and antisera, with a view, in particular, to purifying this protein and fragments thereof. As a corollary thereto, this invention features the use of said polypeptides to produce recombinant antibodies or antibody fragments, regardless of the biological system for obtaining the latter.

In order to further illustrate the present invention and the advantages thereof, the following specific examples are given, it being understood that same are intended only as illustrative and in nowise limitative.

EXAMPLES

Isolation and Characterization of the Polypeptide:

The stratum corneum proteins were collected by the so-called "scraping" method. This technique does not require an extraction phase by an organic solvent and is therefore likely to cause less destruction of the enzymatic activities. It permits, in addition, obtaining a good quantity of material.

The scraping was carried out on the anterior surface of the leg. The area for sample collection was washed with 200 ml of a buffer comprising of 50 mM sodium phosphate buffer, pH 7, 5 mM EDTA, 150 mM NaCl and 0.1% Triton X100, distributed by means of a pump at a constant flow rate of 100 ml/min.

The area was then superficially scraped with the edge of a microscope slide.

The liquid containing the cells was collected in a container situated under the leg.

The buffer thus collected was recycled for numerous passes (15). The samples were then grouped together or otherwise depending on the type of experiment.

The solution thus obtained was first filtered on Whatman No. 4 paper, then on Millipore 0.45 µm filter and finally on Millipore 0.22 µm filter. This clarified solution was concentrated to 12 ml by tangential ultrafiltration with a cut-off of 10 kD at 4° C. with a counterpressure of 1 bar and a filtrate exit flow rate of 2 ml/min by means of the K.BL® apparatus and Sartocon® membranes (Sartorius).

For an individual with healthy skin, the concentration of the proteins extracted by this technique was on the order of 0.15 mg/ml per 12 ml final with 15 passes for the technique.

Separation of the Proteins:

A Superdex G200 HR10/30® column (Pharmacia Biotech) was used for the separation of the proteins with a resolution range extending from 600 kD to 10 kD. This technique, based on separation as a function of the molecular weight, provides a first estimation of the molecular weights of the proteins.

The chromatographic profile obtained evidenced that the protein peaks were predominantly situated towards the low molecular weights (20 to 40 kD).

A column with greater resolving power was then employed. The sample (250 $\mu$l) was injected into a Superdex G75 HR10/30® exclusion column (Pharmacia Biotech) for which the optimum separation was situated at molecular weights ranging from 70 kD to 3 kD.

The column outflow was collected in a 96-well plate, at 4° C., in an amount of 150 $\mu$l/well, after a waiting time of 15 minutes after injection (the latter corresponded to a little less than the dead volume of the column and provided a safety margin for the case where a compound would absolutely not be retained) and a dead volume of 0.24 ml. The output of the pump was 0.5 ml/min, the detection wavelength was 280 nm (Series 10 pump: Perkin Elmer, SP8450 detector: Spectra Physics, LCI-100 integrator: Perkin Elmer, Model 201 fraction collector: Gilson).

The chromatographic profiles obtained on various injections being reproducible, the fractions obtained were mixed "well to well" to provide a working volume of about 800 $\mu$l per fraction.

The various fractions were maintained cold, refrigerator or crushed ice, so as to preserve the enzymatic activities.

The molecular weights corresponding to the various fractions were determined by polyacrylamide gel electrophoresis with an 8%–18% acrylamide gradient. The samples were diluted ¼ in a modified Laemmli buffer (0.0625 M Tris, pH 6.8, 2% SDS and without DTT) and the loadings were 20 $\mu$l. The protein bands were visualized by silver nitrate staining according to the Pharmacia Biotech protocol (kit: silver staining plusone®).

Assay of the Protease Activities:

The protease activities contained in the fractions obtained by transporting over the Superdex G75 HR10/30® exclusion column were assayed by fluorometry using the Enzcheck® kit (Molecular Probes).

This kit is a rapid and simple method of measuring the protease activities, with no precipitation or separation phase and is therefore suitable for rapid screening of the protease activities of the different fractions. This protocol employs, as substrate therefor, BODIPYfl-caséine® which becomes fluorescent after enzymatic digestion. The fluorescence thus liberated is directly proportional to the protease activity contained in the sample. The fluorescence was measured on the LS50B spectrofluorometer, Perkin Elmer, with an excitation wavelength of 485 nm (slit of 2.5 nm), an emission wavelength of 535 nm (slit of 8 nm) and an integration time of 1 second per well.

The assays were carried out in the presence or absence of cysteine at a final concentration of 5 mM so as to detect possible cysteine protease activities.

Figure 1:
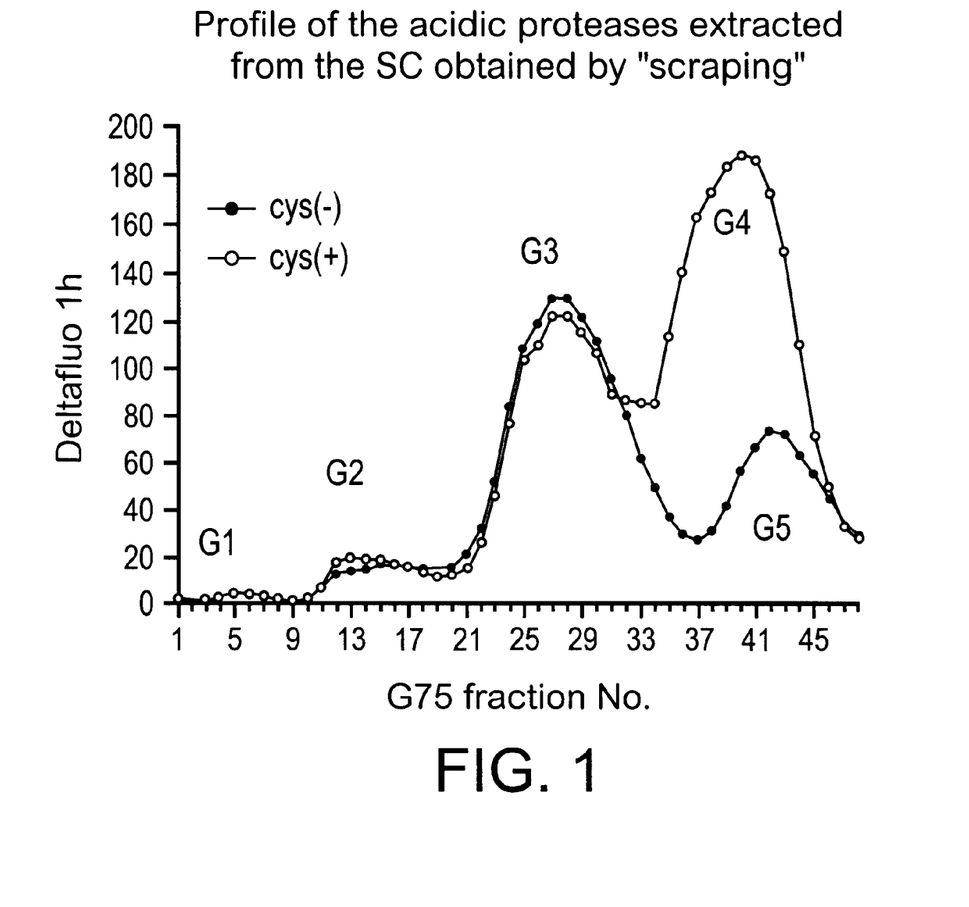
FIG. 1 is a graph reflecting the activity profiles of the proteases contained in protein samples from the stratum corneum in the presence or absence of cysteine.

The results obtained are shown in FIG. 1.

The protease profile revealed the existence of a peak (G4) which was present when the buffer contained cysteine and absent when the buffer did not contain cysteine.

This peak therefore revealed in fractions 34 to 47 the existence of a cysteine-dependent protease. This protease had a molecular weight on the order of 28 kD.

pH Optimum for Activity of the Proteases:

To characterize the pH optimum for activity of the proteases of the G4 peak, two buffers, as described in "Data for Biochemical Research", (Dawson et al., 3rd Edition, Oxford science publications, 1990), were prepared to cover a pH range extending from 4.0 to 8.25:

0.1 M acetate buffer, pH 4.0 to 5.75;

0.1 M phosphate buffer, pH 5.75 to 8.25.

All the buffers contained 5 mM EDTA and 0.1% Triton X100. The activities were measured every 0.25 pH unit.

The above technique for measuring the protease activity was used with each of the 2 buffers, on each fraction.

Figure 2A:
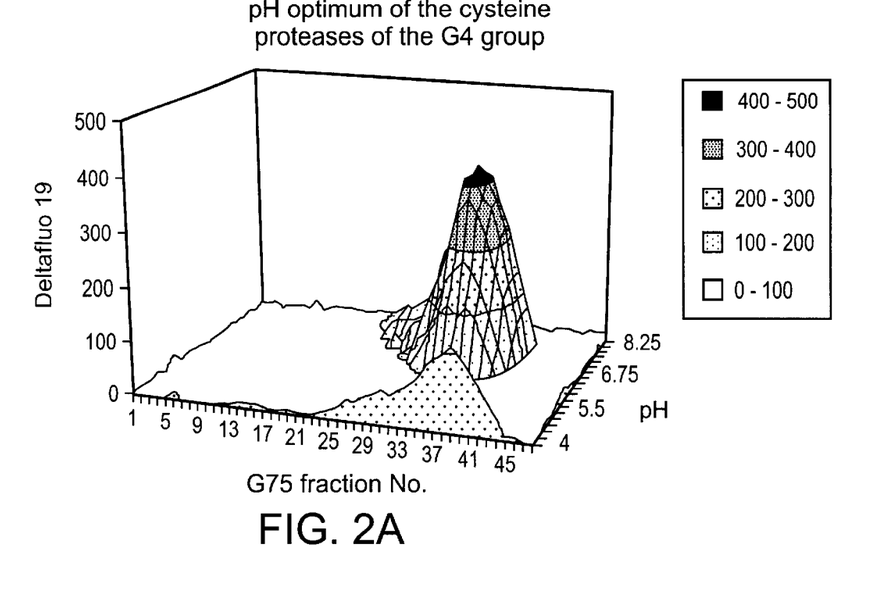
FIG. 2 is a graph reflecting the activity profiles of the proteases of the G4 peak as a function of the pH.
Figure 2B:
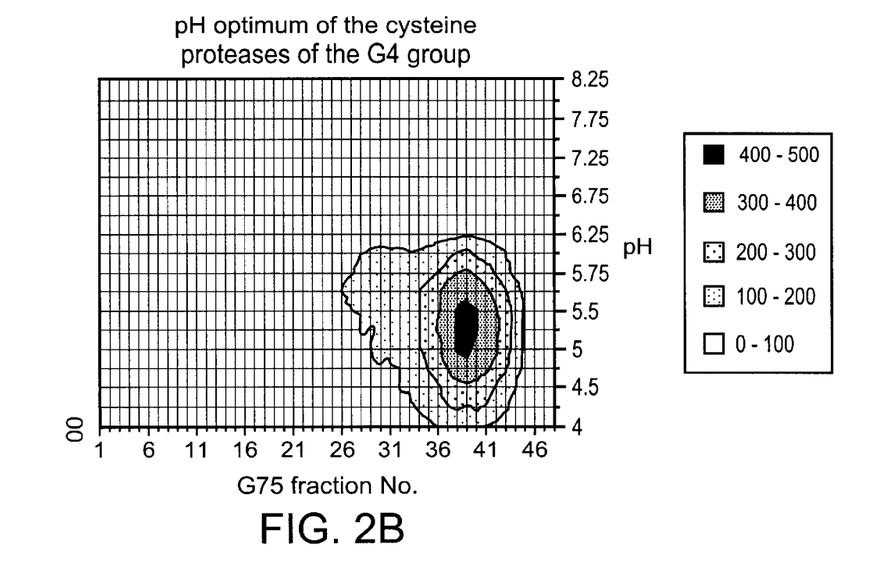

The results obtained are shown in FIG. 2.

The pH optimum for the proteases extracted from the stratum corneum, acting on the substrate BODIPYfl-caséine® was situated at the acidic pH values, from 4.0 to 6.25.

The highest activity was obtained for between pH 5.0 and 5.5 with the acetate buffer. The acetate buffer at pH 5.0 was therefore the buffer used for the remainder of the experiments.

Characterization of the Protease Peaks by the use of Inhibitors:

In order to better characterize the cysteinedependent protease isolated above, tests of inhibition by known protease inhibitors were carried out. The measurements were carried out in an identical manner to the preceding measurements in the presence of cysteine at a final concentration of 5 mM and in the presence or absence (control) of the inhibitor considered.

Inhibitor E 64:

E 64 is an inhibitor of the cysteine proteases and in particular of the cathepsins B, H, L (Proteolitic enzymes: a practical approach, R. J. Beyton and J. S. Bond, IRL press, Oxford, 1989).

The test was carried out at an E 64 inhibitor concentration of 1.4 $\mu$M.

Figure 3:
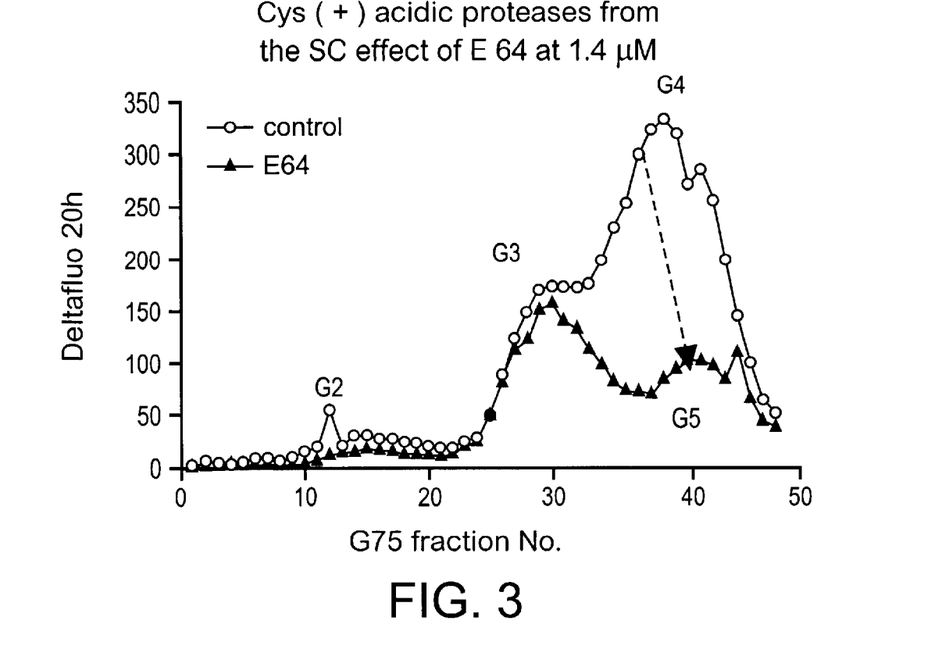
FIG. 3 is a graph reflecting the activity profiles of the proteases of the G4 peak in the presence of the inhibitor E 64 (Proteolytic enzymes: a practical approach, R. J. Beyton and J. S. Bond, IRL press, Oxford, 1989)

The results obtained are shown in FIG. 3.

E 64 at 1.4 $\mu$M inhibited by about 71% the activity of the cysteine-dependent protease of the G4 peak. In the light of the specificity of this inhibitor, G4 was a cathepsin B, H or L.

Leupeptin:

Leupeptin, at the dose employed, was specific for cathepsins B or L and was without effect on the H cathepsins (Schwartz et al., 1980).

The test was carried out at a leupeptin concentration of 1 $\mu$M.

Figure 4:
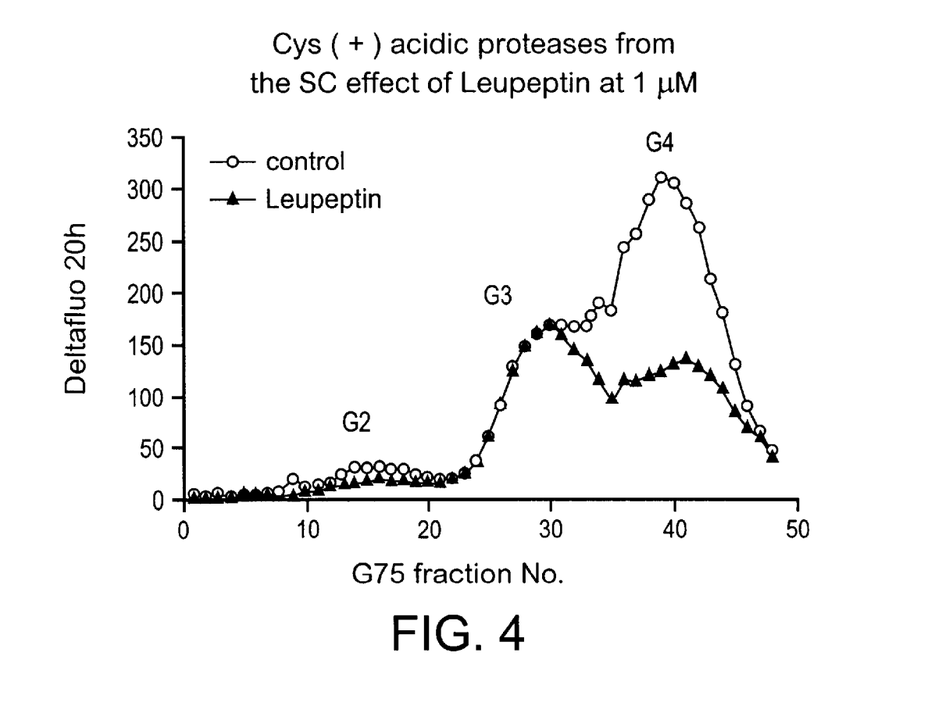
FIG. 4 is a graph reflecting the activity profiles of the proteases of the G4 peak in the presence of leupeptin.

The results obtained are shown in FIG. 4.

Leupeptin at 1 $\mu$M, in the presence of cysteine, reduceed the protease activity of G4 by about 41%.

G4 was not an H cathepsin.

Chyrostatin:

Chymostatin was specific for the L cathepsins and was inactive, at the concentration used, on the B cathepsins (Inubushi et al., J. of Biochemistry, 116, 282–284, 1994).

The test was carried out at a chymostatin concentration of 2.5 $\mu$M.

Figure 5:
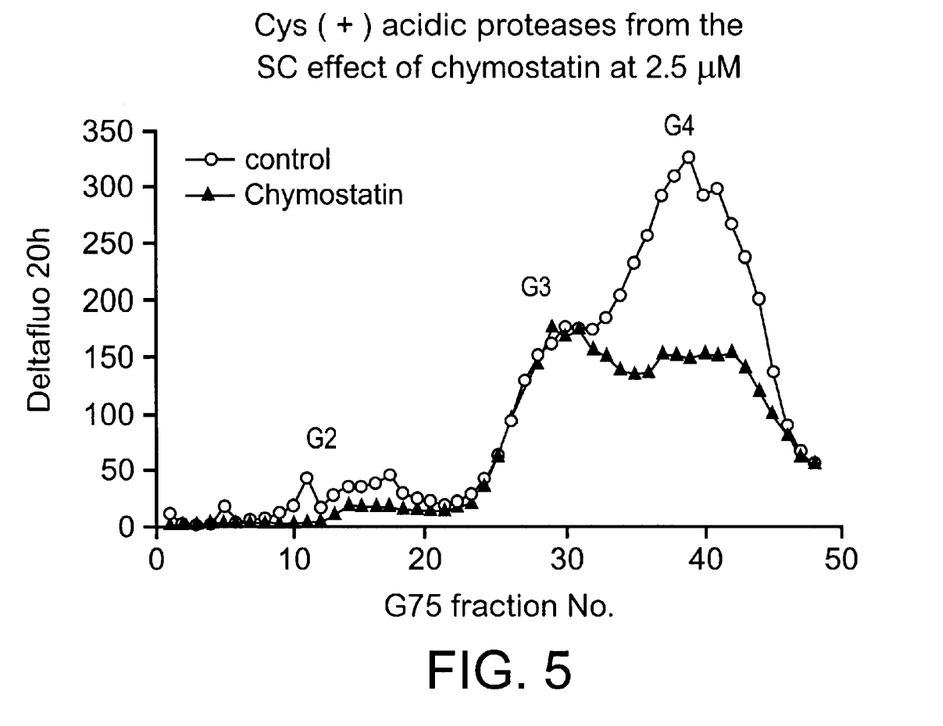
FIG. 5 is a graph reflecting the activity profiles of the proteases of the G4 peak in the presence of chymostatin.

The results obtained are shown in FIG. 5.

Employed at 2.5 $\mu$M, chymostatin inhibited by more than 50% the cysteine-dependent protease of peak G4.

G4 is a cathepsin L type protease.

Inhibitor CA 074:

Inhibitor CA 074 inhibited specifically the B cathepsins and was without action on the L cathepsins (Inubushi et al., 1994).

The test was carried out at a chymostatin concentration of 1 $\mu$M.

Figure 6:
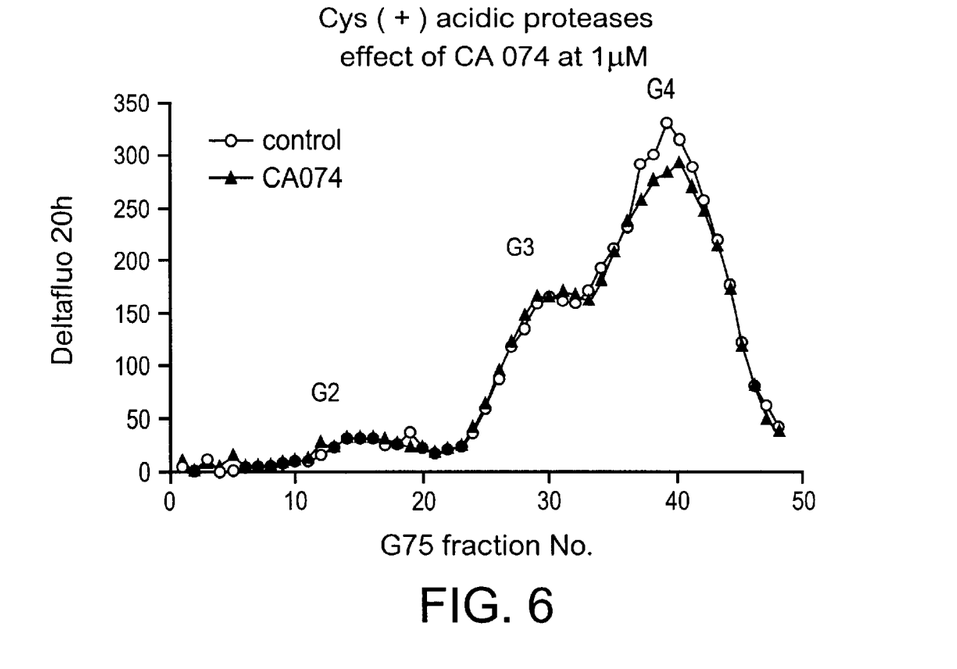
FIG. 6 is a graph reflecting the activity profiles of the proteases of the G4 peak in the presence of the inhibitor CA 074 (Inubushi et al., *J. of Biochemistry*, 116, 282–284, 1994)

The results obtained are shown in FIG. 6. Inhibitor CA 074, practically, did not affect the activity profile of the cysteine-dependent protease of peak G4.

G4 is not a cathepsin B type protease.

Pepstatin:

Pepstatin is an inhibitor specific for aspartic acid proteases (Proteolytic enzymes: a practical approach, R. J. Beyton and J. S. Bond, IRL Press, Oxford, 1989).

The test was carried out at a pepstatin concentration of 1 $\mu$M.

Figure 7:
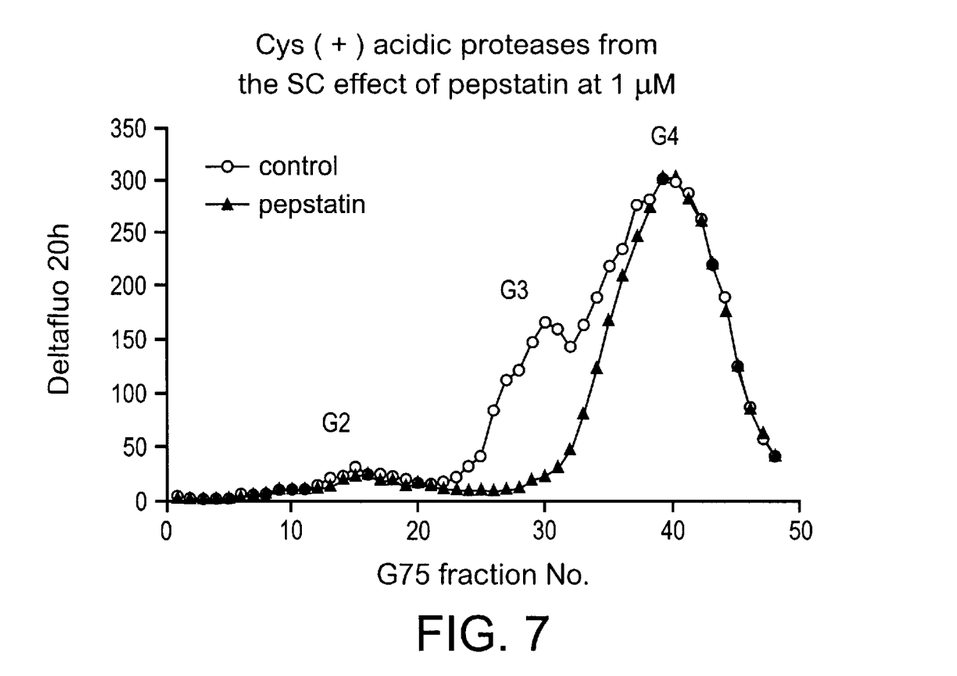
FIG. 7 is a graph reflecting the activity profiles of the proteases of the G4 peak in the presence of pepstatin.

The results obtained are shown in FIG. 7.

Pepstatin was without action on G4. G4 was not an aspartic acid protease.

Use of a Substrate Specific for the L Cathepsins [z (phe-arg 2R110) (Assfalg-Machleidt et al., 1992)]to Confirm the Characterization of G4:

The results of identification of G4, obtained by the different inhibitor tests, were confirmed by the use of a preferred peptide substrate of the L cathepsins, labelled with rhodamine 110. This substrate was 850 times more sensitive to the action of the L cathepsins than of the B cathepsins.

Figure 8:
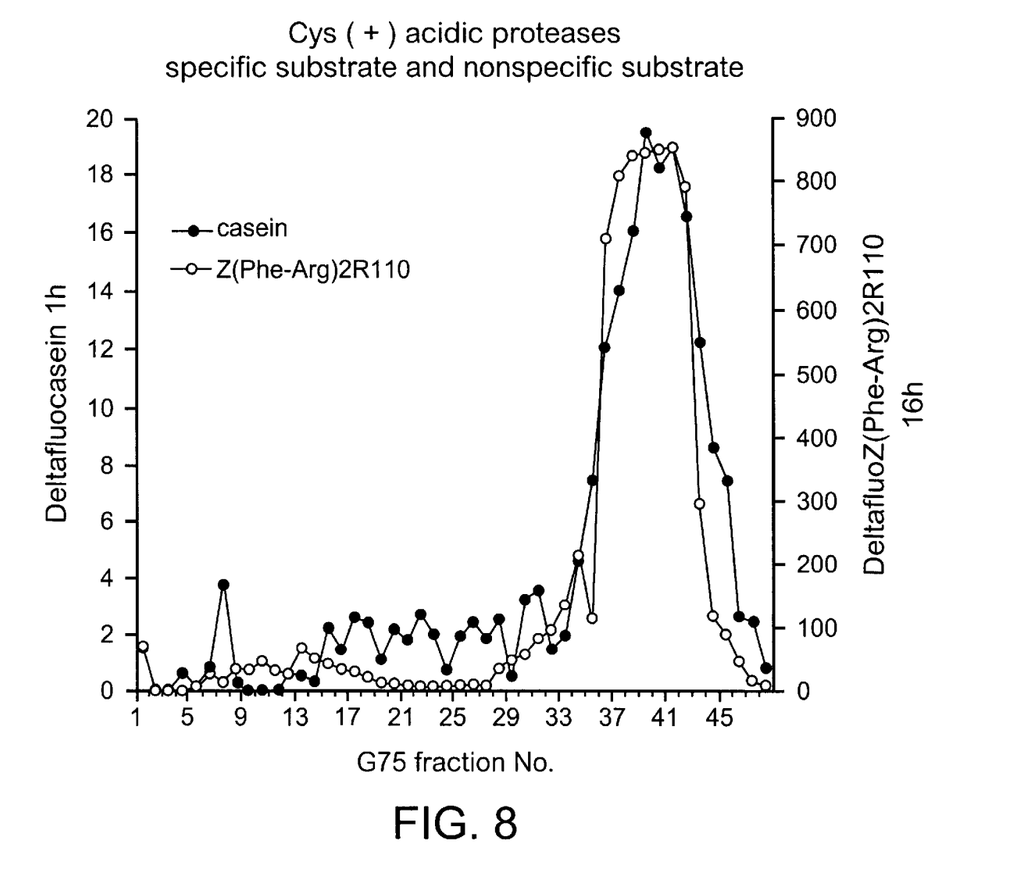
FIG. 8 is a graph reflecting the activity profiles of the proteases of the G4 peak in the presence of a preferred peptide substrate of the L cathepsins.

The results of the evaluation of protease activity in the presence of cysteine, control without cysteine subtracted, are presented in FIG. 8.

The results show that the intense hydrolysis of the specific peptide substrate was perfectly superimposed on that of casein, confirming the cathepsin L nature of G4.

Evaluation of the Aparent Isoelectric Point of G4:

This evaluation was carried out by the chromatofocusing technique as described in "Protein Purification", J-C. Janson and L. Ryden, VCH Publisher Inc. N.Y., 1989, under the following conditions:

Column: Mono PTM HR 5/20 Pharmacia.

Sample: human SC extract equilibrated in 0.075 M Tris/acetate buffer, pH 9.3.

Elution buffer: 10 ml polybuffer 96/acetate, pH 6.0, ("Protein Purification", J-C. Janson and L. Ryden, VCH Publisher Inc. N.Y., 1989).

Flow rate: 1 ml/min.

Fractions: 0.5 ml from the injection on 48 ml total.

Detection: Cathepsin L activities on 10 mM Z(phe-Arg) 2R110 in 0.1 M acetate buffer pH 5.0, 0.1% Triton X100, 5 mM EDTA, 5 mM cysteine. Incubation of 10 $\mu$l of fraction+ 200 $\mu$l of substrate at 37° C. for 2 h, 30 min. Reading on Biolumin® from Molecular Dynamics in which the photomultiplier was set at 700 V, excitation: 485/10 nm, emission: 520/10 nm.

Figure 9:
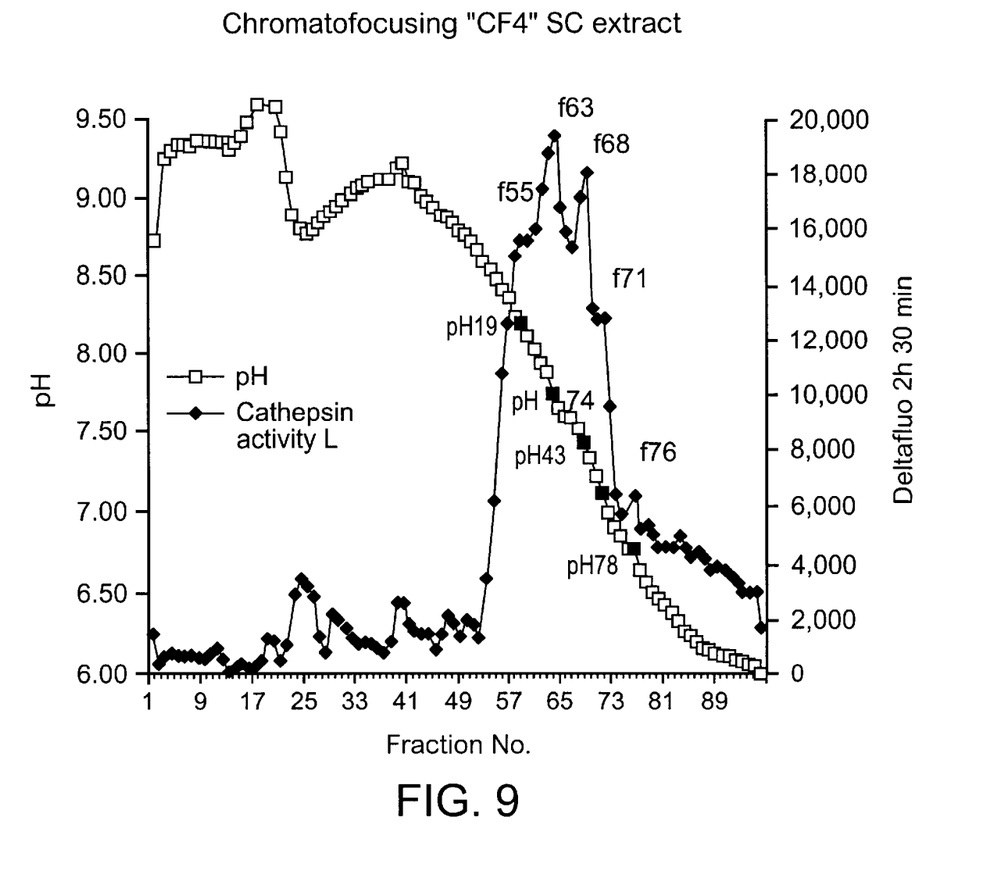
FIG. 9 is a graph reflecting the profiles obtained during chromatofocusing experiments for the determination of the apparent isoelectric point.

The results obtained are presented in FIG. 9.

These results evidence an apparent isoelectric point of between 6 and 9.

Demonstration of the Probable role of G4 in the Desquamation Process:

Corneodesmosine is an essential protein in the corneodesmosome which is degraded during desquamation (Serre G. et al., J.I.D., 1991, 97(6), 1061–1072).

The test was performed on corneodesmosine extracted from the stratum corneum according to the technique developed by Munerot C. (DEA report, 1996, Marne la Vallée University).

An immunotransfer performed on corneodesmosine after incubation on whole stratum corneum in the presence or absence of the G4 peak protease showed a pronounced degradation thereof.

The G4 peak protease present in the stratum corneum degraded corneodesmosine.

All of the results of the tests carried out evidenced that the polypeptide extracted from the stratum corneum was a cathepsin L type cysteine-dependent protease having an apparent molecular weight of about 28 kD and an isoelectric point ranging from 6 to 9.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An isolated, substantially pure cathepsin L type cysteine protease which is present in healthy stratum corneum contained in the cornified layer of the skin and having an apparent molecular weight ranging from 25 to 30 kilodaltons.

2. The cysteine protease polypeptide as defined by claim 1, having an isoelectric point ranging from 6 to 9.

3. The cysteine protease polypeptide as defined by claim 1, wherein said protease is isolated from mammalian tissue.

4. The cysteine protease polypeptide as defined by claim 3, wherein said mammalian tissue is mammalian skin tissue.

5. The cysteine protease polypeptide as defined by claim 4, wherein said mammalian skin is tissue human skin tissue.

6. The cysteine protease polypeptide as defined by claim 5, wherein said human skin tissue is human epidermis.

7. The cysteine protease polypeptide as defined by claim 1, exhibiting activity at a pH ranging from 2 to 9.

8. The cysteine protease polypeptide as defined by claim 7, exhibiting activity at a pH ranging from 3.5 to 6.5.

9. The isolated, substantially pure, cathepsin L type cysteine protease of claim 1, which exhibits activity at a pH ranging from 4 to 6.25.

10. The cysteine protease of claim 9, which exhibits optimal activity at pH ranging from 5 to 5.5.

11. The cysteine protease of claim 1, which possesses a molecular weight of about 28 kilodaltons.

* * * * *